United States Patent

Bertin et al.

[11] Patent Number: 5,908,424
[45] Date of Patent: Jun. 1, 1999

[54] TIBIAL MILLING GUIDE SYSTEM

[75] Inventors: Kim C. Bertin, Bountiful, Utah; Robert Booth, Jr., Philadelphia, Pa.; Dennis W. Burke, Milton, Mass.; Rodney Bays, Pierceton, Ind.; Terry L. Dietz; Gregory C. Stalcup, both of Columbia City, Ind.; Richard D. Vanlaningham, Milford, Ind.

[73] Assignee: Zimmer, Inc, by said Stalcup, Dietz, Bays and Vanlaningham, Warsaw, Ind.

[21] Appl. No.: 08/242,987

[22] Filed: May 16, 1994

[51] Int. Cl.$^6$ ................................................. A61B 17/56
[52] U.S. Cl. .................................... 606/88; 606/96
[58] Field of Search .................... 606/88, 87, 90, 606/89, 96, 97, 98, 102, 79, 80, 82, 84, 85, 86; 408/241 G; 407/30, 33, 36, 44, 53, 54; 409/125, 130, 205, 218

[56] References Cited

U.S. PATENT DOCUMENTS

| | | | |
|---|---|---|---|
| 4,457,307 | 7/1984 | Stillwell | 606/88 X |
| 4,524,766 | 6/1985 | Petersen . | |
| 4,567,886 | 2/1986 | Petersen | 606/88 X |
| 4,574,794 | 3/1986 | Cooke et al. | 606/88 X |
| 4,625,405 | 12/1986 | Hudnutt et al. | 30/370 |
| 4,721,104 | 1/1988 | Kaufman et al. . | |
| 4,841,975 | 6/1989 | Woolson | 128/653 |
| 4,935,023 | 6/1990 | Whiteside et al. | 606/88 |
| 4,938,762 | 7/1990 | Wehrli | 606/88 |
| 4,952,213 | 8/1990 | Bowman et al. | 606/79 |
| 5,002,547 | 3/1991 | Poggie et al. | 606/88 |
| 5,007,912 | 4/1991 | Albrektsson et al. | 606/87 |
| 5,035,699 | 7/1991 | Coates | 606/86 |
| 5,049,149 | 9/1991 | Schmidt | 606/87 |
| 5,098,436 | 3/1992 | Ferrante et al. | 606/88 |
| 5,141,513 | 8/1992 | Fortune et al. | 606/96 |
| 5,176,684 | 1/1993 | Ferrante et al. | 606/86 |
| 5,190,547 | 3/1993 | Barber et al. | 606/79 |
| 5,197,944 | 3/1993 | Steele | 606/27 |
| 5,207,680 | 5/1993 | Dietz et al. | 606/86 |
| 5,250,050 | 10/1993 | Poggie et al. | 606/79 |
| 5,304,181 | 4/1994 | Caspari et al. | 606/80 |
| 5,306,276 | 4/1994 | Johnson et al. | 606/86 |
| 5,344,423 | 9/1994 | Dietz et al. | 606/87 |
| 5,417,695 | 5/1995 | Axelson, Jr. | 606/89 |

FOREIGN PATENT DOCUMENTS 577020  10/1977  Russian Federation ............ 606/88

OTHER PUBLICATIONS

Scott et al. "PFC Modular Knee System with Specialist Instruments" Johnson & Johnson Orthopaedics Brochure, pp. 18–27.

Primary Examiner—Guy V. Tucker
Attorney, Agent, or Firm—Todd A. Dawson

[57] ABSTRACT

A tibial milling guide which incorporates a combination of instruments for producing a planar surface on a portion of the tibia using a milling device. The system includes: an extramedullary alignment guide with a detachable reference guide, an adjustable milling base assembly, a detachable milling template, a sizing gauge, and a milling depth gauge. The reference guide is used to position the alignment guide to the tibia. The reference guide has a T-shaped member which provides a planar reference and a centering reference to the tibial head. The reference guide also allows the surgeon to set the rotational alignment before the alignment guide is secured in place. The adjustable milling base assembly is also detachably connected to the alignment guide. The milling base assembly includes a slide and a shiftable base that allows for lateral adjustments of the template with respect to the articular surface after the alignment guide has been properly secured to the tibia. The milling base is also extensibly connected to the alignment guide to allow the spacing between the articular surface and the template to be adjusted.

16 Claims, 9 Drawing Sheets

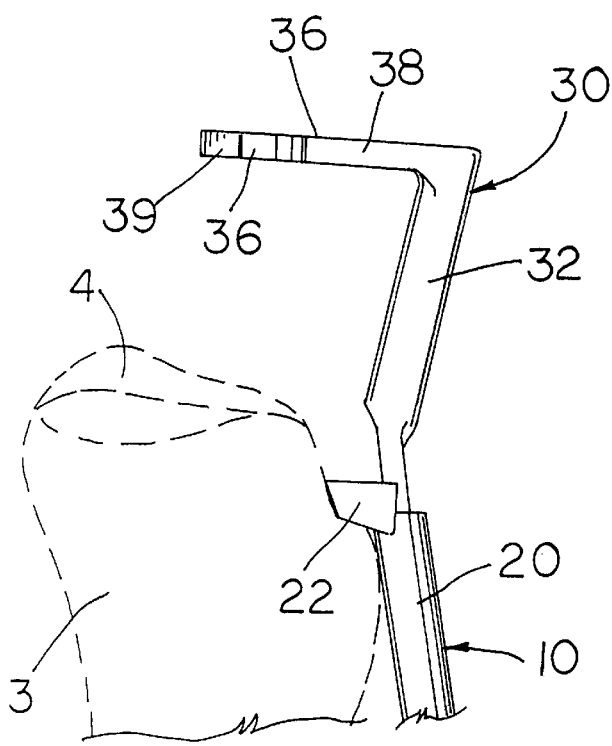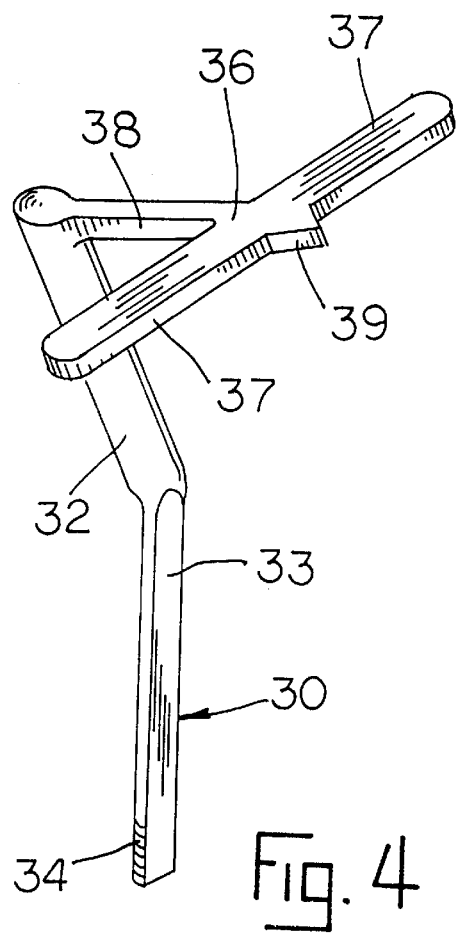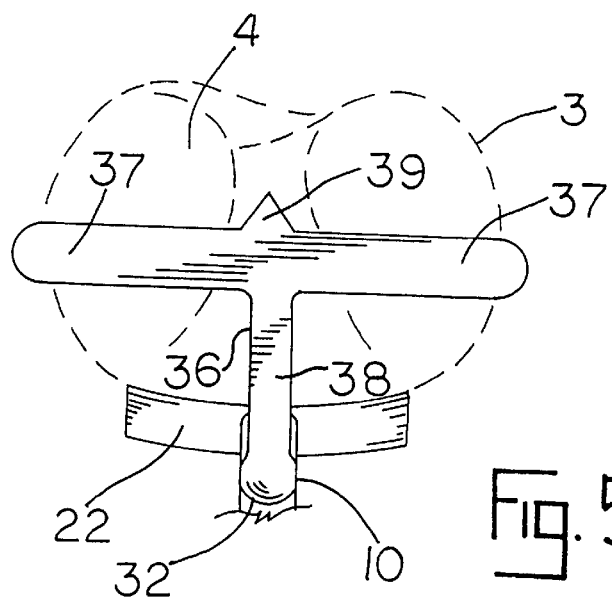

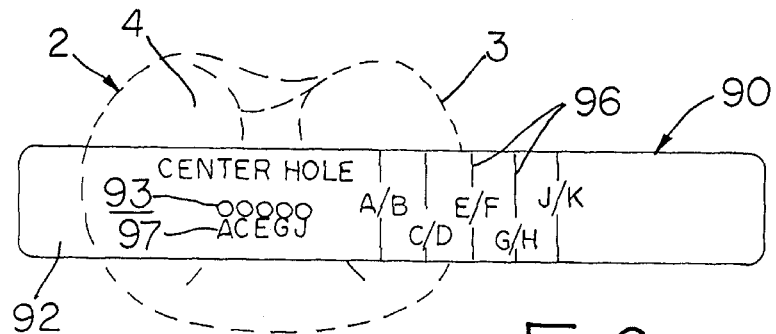
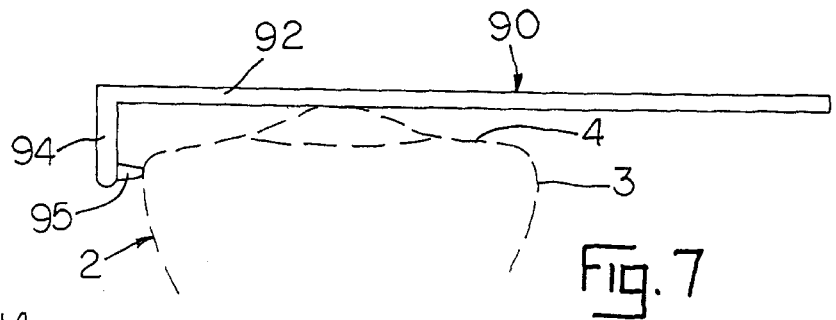
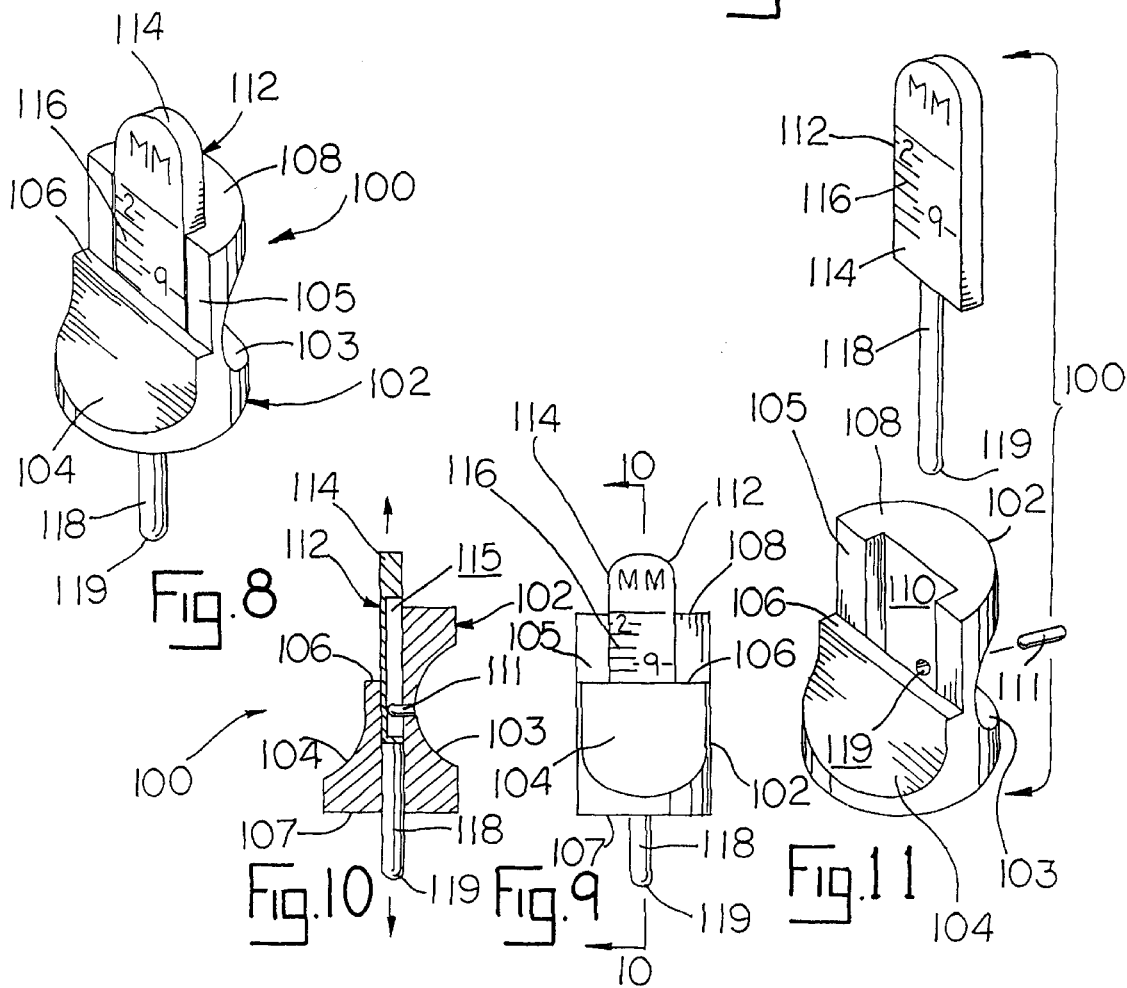

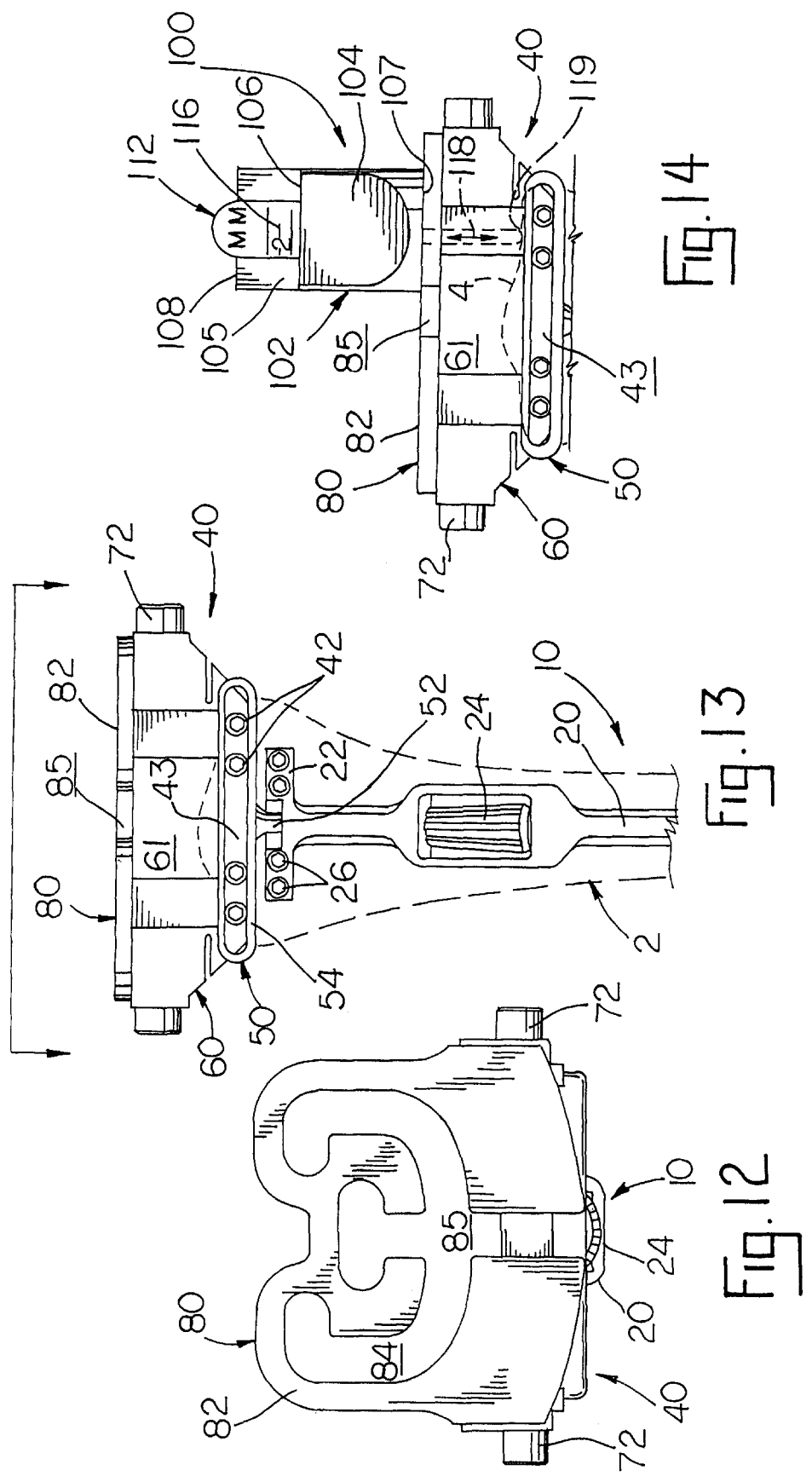

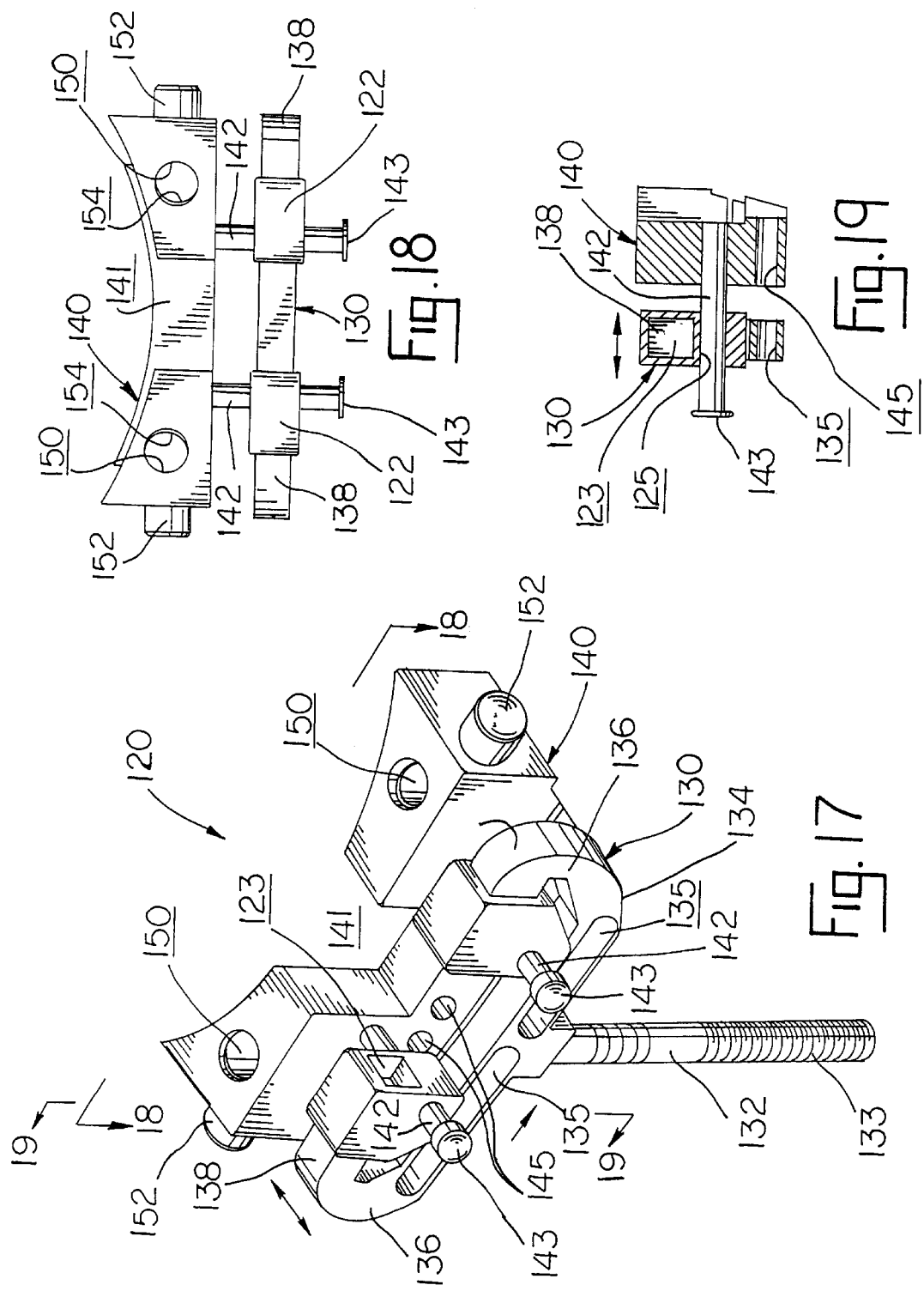

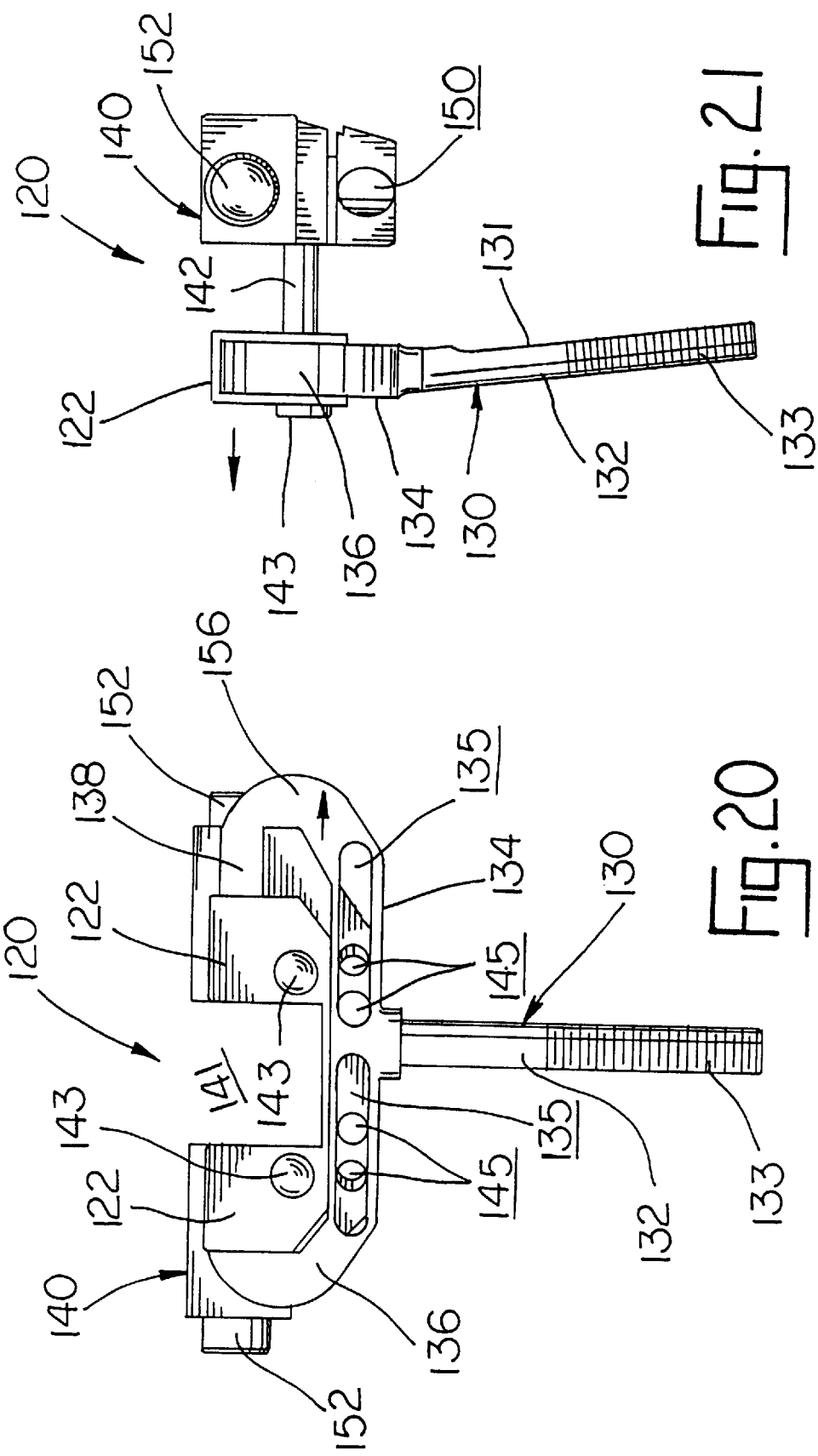

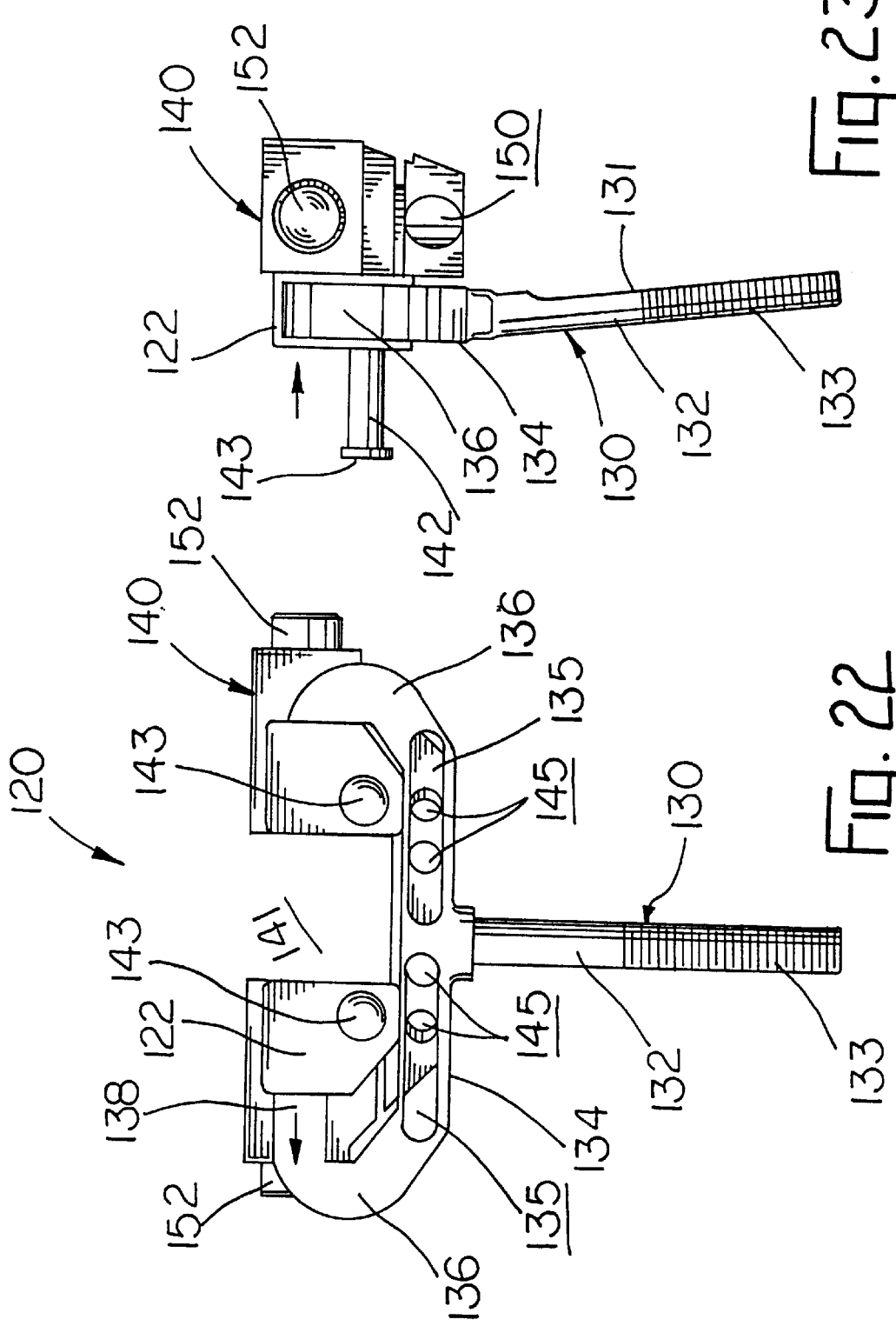

TIBIAL MILLING GUIDE SYSTEM

This invention relates to a system of instruments used for cutting bone and has specific relevance to a system of instruments for cutting a planar surface on a portion of bone using a milling device.

BACKGROUND OF INVENTION

Surgical procedures for removing a defective joint and replacing it with a prosthetic joint are well known. Removal of a portion of bone tissue is often necessary to accommodate the prosthetic joint. Conventional bone cutting methods have employed reciprocating saws and guide instruments which align and guide the saw blade to produce the desired cut. Conventional guide instruments must be properly aligned and affixed to the bone itself in order to assure that the cutting process will produce a suitable articular surface for the attachment of the prosthetic joint. Once the cutting guide is properly aligned and affixed to the bone, small adjustments to the alignment and position of the guide instrument with respect to the bone are often desirable.

Milling devices have been developed to mill articular surfaces on bone. Heretofore, the milling devices use alignment guide instruments which are affixed to the bone to position and guide the milling device over the bone surface. Generally, the milling guide instruments include templates which have a track to accommodate the shaft of the milling device. Again, once the milling guide instruments are aligned and attached, lateral adjustments are often desired, and conventional milling guide instruments must be realigned and reattached to accommodate fine adjustments.

SUMMARY OF INVENTION

The tibial milling guide system of this invention incorporates a set of instruments for producing a planar surface on the proximal end of the tibia using a milling device. The system includes: an extramedullary alignment guide with a detachable reference guide, an adjustable milling base assembly, a detachable milling template, a sizing gauge, and a milling depth gauge.

The extramedullary alignment guide of this invention has a conventional telescoping design which is adjustable both in length and attitude to the tibia. The upper portion of the alignment guide is secured to the exposed tibia by bone screws or similar fasteners and the lower portion is secured to the lower leg by a plate and a connecting strap. The extramedullary alignment guide is aligned on the tibia by a detachable reference guide which is extensibly connected to the upper portion of the guide. The reference guide has a T-shaped member which provides a planar reference and centering reference relative to the articular surface of the tibia. The reference guide also allows the surgeon to set the rotational alignment before the alignment guide is secured in place. Once the alignment guide is secured, the reference guide is removed and the adjustable milling base is connected to the alignment guide.

The milling base assembly supports a milling template over the articular surface of the tibial head. The template has a reference surface which determines the milling depth and a track which accommodates the shaft of the milling device and constitutes the travel path of the milling device.

The adjustable milling base assembly includes a slide and a shiftable base. The slide is extensibly connected to the alignment guide to allow the spacing between the template and the articular surface to be adjusted. The base is shiftably connected to the slide to allow for lateral adjustments of the template with respect to the articular surface after the alignment guide has been properly secured to the tibia. In one embodiment, the base is connected to the slide for unilateral movement parallel to the articular surface. In a second embodiment the base is shiftably connected to the slide for bi-lateral movement parallel to the articular surface.

The system includes a milling depth gauge and a sizing gauge The depth gauge indicates to the surgeon the milling depth the template is positioned at. The depth gauge includes a body and an extensible indicator which passes axially through the gauge body. The gauge body is positioned on the reference surface of the template with the contact end of the indicator passing through the template track to engage the tibia. A depth reading can be obtained from the portion of the indicator which extends above the gauge body. The sizing gauge is used to determine the appropriate size of the template.

Accordingly, an advantage of this invention is to provide for a system of instruments for producing a planar cut using a milling device.

Another advantage of the invention is to provide a milling base assembly used with an extramedullary tibial alignment guide which allows for uni-lateral adjustment of a milling template with respect to the articular surface of a tibial head.

Another advantage of the invention is to provide a milling base assembly used with an extramedullary tibial alignment guide which allows for bi-lateral adjustment of a milling template with respect to the articular surface of a tibial head.

Another advantage of the invention is to provide for a reference guide for use with an extramedullary tibial alignment guide.

Another advantage of the invention is to provide for a sizing gauge for a bone.

Another advantage of the invention is to provide for a depth gauge for indicating the depth of a milling cut for a bone.

Other advantages will become apparent upon a reading of the following description.

BRIEF DESCRIPTION OF THE DRAWINGS

A preferred embodiment of the invention has been depicted for illustrative purposes only wherein:

FIG. 3 is a side view of the reference guide and alignment guide showing the position of the reference guide with respect to a tibial head.

FIG. 4 is a perspective view of the reference guide.

FIG. 5 is a top view of the reference guide and alignment guide showing the position of the reference guide with respect to a tibial head (shown in broken lines).

FIG. 6 is a top view of the sizing gauge shown in relation to a tibial head (shown in broken lines).

FIG. 7 is a side view of the sizing instrument shown in relation to a tibial head (shown in broken lines).

FIG. 8 is a perspective view of the milling depth gauge of this invention.

FIG. 9 is a front view of the milling depth gauge.

FIG. 10 is a sectional view of the milling depth gauge taken along line 10—10 of FIG. 9.

FIG. 11 is an exploded view of the milling depth gauge.

FIG. 12 is a top view of a template seated atop the adjustable milling base assembly and alignment guide.

FIG. 13 is a partial front view of the template, adjustable milling base assembly and the upper portion of the alignment guide connected to the tibia (shown in broken lines).

FIG. 14 is a front view of the depth gauge positioned on a template and adjustable milling base assembly.

FIG. 17 shows a second embodiment of the adjustable milling base assembly.

FIG. 18 is a top view of the adjustable milling base assembly of FIG. 17.

FIG. 19 is a sectional view of the adjustable milling base assembly taken along line 19—19 of FIG. 18.

FIG. 20 is a front view of the adjustable milling base of FIG. 17 with the base shifted to one side of the slide head.

FIG. 21 is a side view of the adjustable milling base of FIG. 17 with the base shifted away from the slide head.

FIG. 22 is a front view of the adjustable milling base of FIG. 17 with the base shifted to the opposite side of the slide head.

FIG. 23 is a side view of the adjustable milling base of FIG. 17 with the base shifted to abut the slide head.

DESCRIPTION OF THE PREFERRED EMBODIMENT

Figure 1:
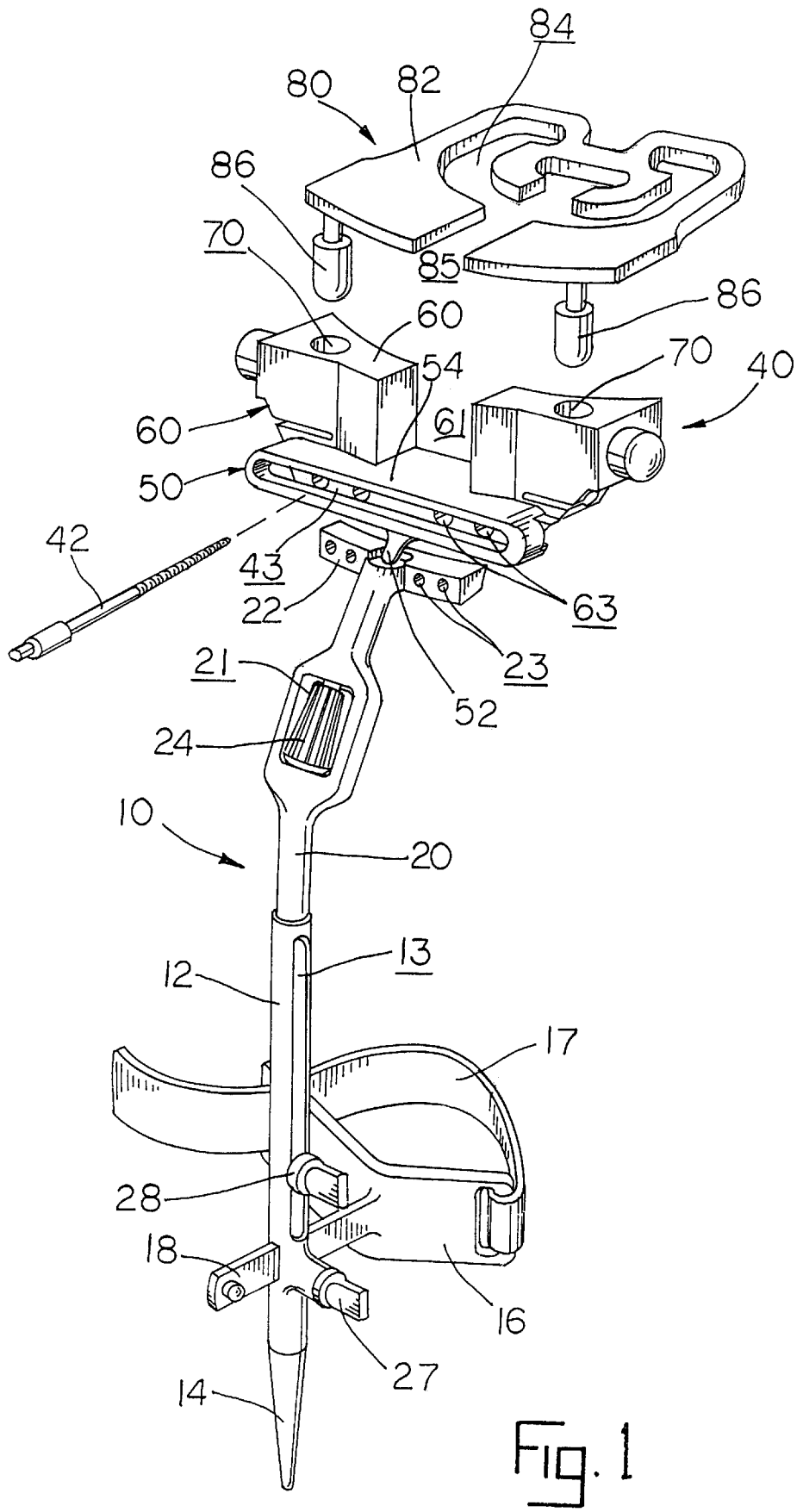
FIG. 1 is a front perspective view of the extramedullary alignment guide, a template and one embodiment of the adjustable milling base assembly of this invention.

The preferred embodiments herein described are not intended to be exhaustive nor to limit the invention to the precise forms disclosed. They are chosen and described to explain the principles of the invention and its application and practical use to enable others skilled in the art to utilize its teachings.

FIGS. 1–16 show the tibial milling guide system of this invention. The tibial milling guide system has a variety of separate components including: an extramedullary tibial alignment guide 10; an adjustment milling base assembly 40; a milling template 80; a sizing gauge 90; and a milling depth gauge 100. All of the separate components are constructed of suitable materials that allow the components to be reusable and sterilized.

Extramedullary Alignment Guide

Figure 2:
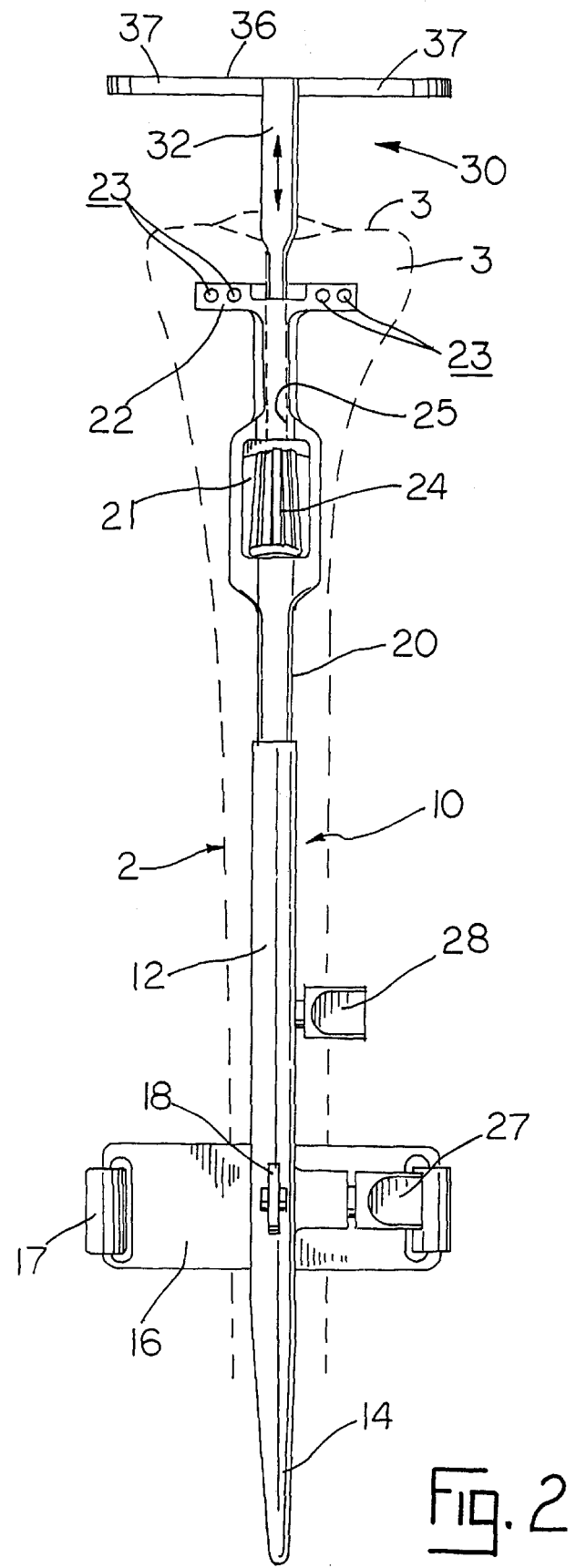
FIG. 2 is a front view of the extramedullary alignment guide and the reference guide shown with respect to a tibia (shown in broken lines).

As shown in FIGS. 1 and 2, extramedullary tibial alignment guide 10 is of conventional telescoping design and includes an extensible upper member 20 shiftably fitted within a tubular lower member 12. Lower member 12 has a longitudinal slot 13 and terminates in a pointed end 14. Lower member 12 includes an adjustable plate 16 and connecting strap 17 for securing the lower member to the patient's lower leg. Plate 16 is arcuate to conform to the outer contour of a patient's lower leg adjacent the ankle. Plate 16 includes a perpendicular slide member 18. Slide member 18 extends laterally through lower member 12 and is secured by lock screw 27 to adjustably connect plate 16 and lower member 12.

Upper member 20 has a solid elongated body which terminates in a perpendicular mounting bracket 22. Bracket 22 has a plurality of bores 23 for accepting bone screws 16 which secure upper member 20 to the proximal tibia (shown in FIGS. 13, 14, and 16). Upper member 20 also has a central opening 21. A vertical adjustment knob 24 is supported within opening 21, as shown in FIG. 1. Vertical adjustment knob 24 has a threaded longitudinal through bore (not shown). A semicircular longitudinal bore 25 extends through upper member 20 from its upper end to opening 21. Upper member 20 is secured within lower member 12 by a length adjustment lock screw 28 which extends through a groove 13 and threads into a bore in upper member 20.

As commonly used in the art, the length and attitude of alignment guide 10 can be adjusted and secured using lock screws 27 and 28. The length of alignment guide 10 can be adjusted by selectively telescoping upper member 20 inside lower member 12 and securing them with lock screw 28. The attitude of alignment guide 10 to tibia 2 can also be adjusted by spacing shin plate 16 from the lower member 12 and securing them with lock screw 27. The adjustment of the attitude of the alignment guide establishes the anterior-posterior slope for the milling guide.

Reference Guide

As shown in FIGS. 2–5 alignment guide 10 also includes a detachable proximal tibial reference guide 30. Reference guide 30 includes a neck 32 and a T-shaped member 36. Generally, T-shaped member 36 extends perpendicularly from the upper end of neck 32. T-shaped member 36 is substantially planar and includes two lateral arms 37 extending from a central leg 38 and a centering point 39. The lower portion of neck 32 is adapted to be fitted within bore 25 of alignment guide 10 and has a semicircular cross section with a flat face 33 and a threaded distal end 34. As shown in FIG. 2, reference guide 30 is inserted into bore 25 of upper member 20 with threaded end 34 turned into vertical adjustment knob 24. Consequently, rotating the vertical adjustment knob extends and retracts the reference guide within the alignment guide to adjustably space the T-shaped member above the articular surface of the tibial head.

Adjustable Milling Base

Figure 15:
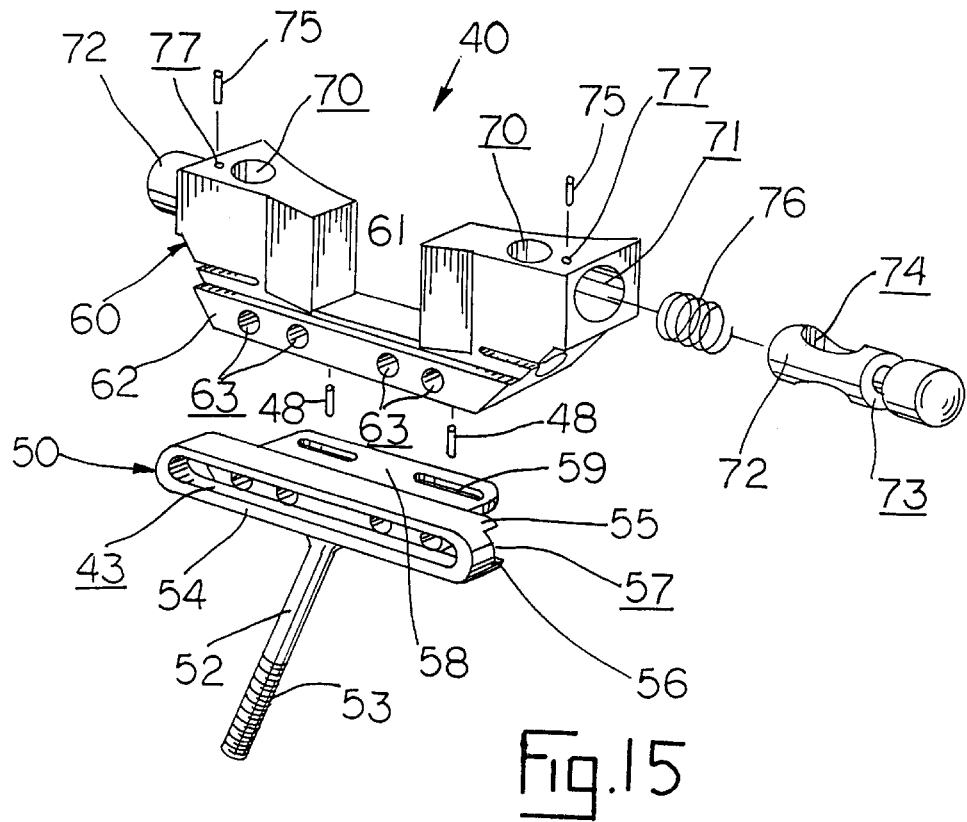
FIG. 15 is an exploded view of the adjustable milling base assembly.

As best shown in FIG. 15, adjustable milling base assembly 40 includes a T-shaped slider 50 and a shiftable base 60. Slide 50 includes a laterally elongated head 54 and an elongated neck 52 extending perpendicularly from head 54. Neck 52 is adapted to be fitted within bore 25 of alignment guide 10 and has a semicircular cross section and a threaded distal end 53. Slide head 54 has an elongated lateral opening 43 which extends in an anterior-posterior direction relative to the tibia. Slide head 54 has a lateral channel 57 defined by an upper posterior flange 55 and a lower posterior flange 56. A slide plate 58 extends from the posterior side of slide head 54 adjacent lower flange 56. A pair of aligned slots 59 are defined in slide plate 58 as shown in FIG. 15.

Shiftable base 60 has a slightly arcuate posterior face to conform to the anterior contour of tibial head 3 just below the knee joint. Base 60 also has a burr opening 61 to allow the burr 7 of the milling device to pass. The anterior face of base 60 has a raised lateral shoulder 62. Transverse through bores 63 are formed in base 60 across shoulder 62 for accommodating bone screws 42 to secure base 60 when properly positioned against the tibia.

Figure 16:
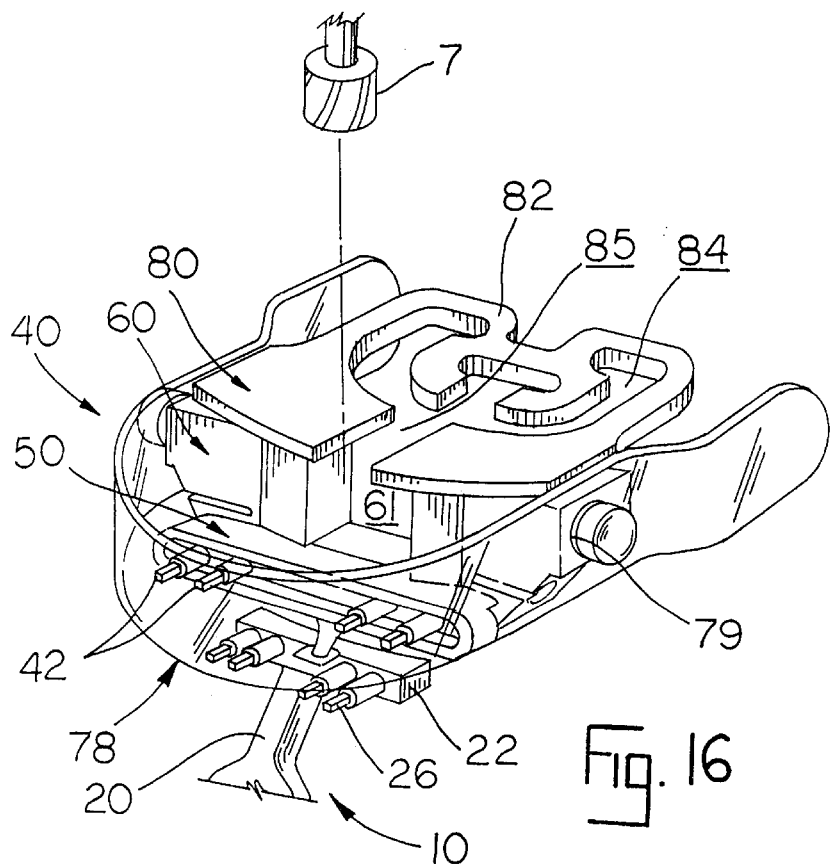
FIG. 16 is a perspective view of a deflector shield attached to the adjustable milling base assembly.

Base 60 is shiftably connected to slide 50. Base 60 is seated atop slide plate 58 with shoulder 62 fitted within channel 57. Stop pins 48 are inserted into holes (not shown) in the lower face of head 54 to protrude into slots 59 of slide plate 58. Stop pins 48 limit the longitudinal movement base 60 along slide head 54. As shown in FIGS. 13, 14 and 16, bore 63 aligns with opening 43 in slide head 54 when base 60 is connected to slide 50. The width of opening 43 is sufficient to allow access to bore 63 when base 60 is shifted to either lateral extreme.

As shown in FIG. 15, base 60 also has a pair of template mounting bores 70 and a release mechanism for securing template 80 to base 60. The release mechanism includes two depressible release cylinders 72 shiftably housed within two end bores 71. Each release cylinder 72 has a lateral through bore 74 normal to its axis and an annular recess 73. Lateral bores 74 of release cylinders 72 have substantially identical diameters as mounting bores 70 and substantially align with mounting bore 70 when release cylinders 72 are inserted into end bore 71. Lock pin 75 extends through a bore 77 in the posterior face of base 60 and into annular release 73 to prevent cylinders 72 from being removed from end bore 71. Springs 76 are inserted into each end bore 71 to urge its release cylinder 72 out from end bore 71, which displaces the alignment of lateral bore 74 and mounting bore 70. Depressing cylinder 72 into end bore 71 axially realigns lateral bores 74 and mounting bores 70.

As shown in FIG. 1, milling base assembly 40 is extensibly connected to alignment guide 10. Neck 52 of slide 50 is inserted into bore 25 of upper member 20 with threaded end 53 turned into vertical adjustment knob 24. Consequently, rotating vertical adjustment knob 24 extends and retracts milling base assembly 40 within upper member 20. The semicircular cross section and flat face of neck 52 keeps the milling base assembly properly aligned within bore 25 when fitted to the alignment guide.

Shield

As shown in FIG. 16, adjustable milling base 40 may include a detachable debris shield 78. Shield 78 has an arcuate transparent body with a pair of side holes 79. Once milling template 80 is attached to the milling base assembly 40, shield 78 can be mounted to base 60 with the protruding ends of release cylinders 72 extending through side holes 79. The resilience of the shield body holds the shield in place. The shield covers the front of the milling base assembly to limit the scattering of tissue debris discharged during the milling process.

Milling Template

Milling template 80 is generally planar and has an upper reference surface 82 and a lower surface 83. Template 80 also has a fixed track 84 and a burr opening 85 for guiding the burr 7 (FIG. 16) of the milling device. Track 84 is shaped so that a portion of the path that burr 7 cuts overlaps other portions of the path to cut a continuous planar surface. Burrs having different diameters may require different track configurations. Reference surface 82 controls the depth of the cut.

While the burr may be guided to cut an area that is within the periphery of the template or an area that extends beyond the template, it is preferable that the periphery of the template correspond to the outer limits of the path cut by the burr to allow an operator to determine the precise location where tissues will be cut. It is also preferable to provide a variety of guides to accommodate a variety of bone sizes and shapes and a variety of shape cut areas. The exemplary guide shown provides an uncut posterior region as would be suitable for a posterior crucial ligament retaining tibial prosthesis.

Two mounting posts 86 extend from the lower surface 83 for connecting template 80 within mounting bores 70 of base 60. Mounting posts 86 extend through mounting bores 70 and lateral bore 74 of release cylinder 72. When mounting posts 86 are inserted into base 60, the tension of spring 76 urges release cylinder 72 laterally against mounting posts 86 to secure the template 80 to base 60.

Application

The procedure using the tibial milling guide system of this invention, begins with preparing the knee joint and exposing the tibial head 3. Alignment guide 10 is first fitted with reference guide 30 as shown in FIG. 2. Initially, the lower member 12 of alignment guide 10 is secured to the patient's lower leg. Plate 16 abuts the front of the shin and is secured by strap 17 with point end 14 positioned at the base of the ankle. With lower member 12 of alignment guide 10 secured, the length of the alignment instrument can be adjusted by lock screw 28. Upper member 20 is extended or retracted such that bracket 22 is positioned just below the knee joint.

Reference guide 30 is used to properly position alignment guide 10 along the lower leg. As shown in FIG. 5, rotational alignment is determined by positioning alignment guide 10 so that centering point 39 generally overlies the center of tibial head 3 and each arm 37 of T-shaped member 36 generally extends equidistantly beyond a lateral extremity of tibial head 3. Planar T-shaped member 36 also provides a reference plane for adjusting the attitude of the alignment guide using lock screw 27 so that the proper posterior slope can be established.

Reference guide 30 can be spaced toward and away from the tibial head using vertical adjustment knob 24 to allow improved visual alignment. Once properly aligned, bone screws 26 are driven through bores 23 to secure upper member 20 of alignment guide 10 to tibia 2 as shown in FIG. 2.

With alignment guide 10 properly secured to the tibia and lower leg, reference guide 30 is removed and adjustable milling base 40 is fitted to alignment guide 10. Neck 52 is inserted into bore 25 and threaded end 53 is turned into vertical adjustment knob 24 until milling base assembly 40 is at the appropriate height above articular surface 4. With milling base assembly 40 positioned at the proper height, the surgeon can manually shift base 60 laterally with respect to slide 50 to center base 60 with articular surface 4. Once base 60 is properly positioned, base 60 is secured in place by bone screws 26 which are inserted through opening 43 and bores 63 and turned into tibia 2. After base 60 is secured to the tibia, template 80 is mounted to base 60. Mounting posts 86 are seated within mounting bores 70 with release cylinder 72 locking template 80 to base 60. As shown in FIG. 16, burr opening 85 of template 80 aligns with burr opening 61 of base 60 to allow the burr 7 of a milling device to pass. Optionally, shield 78 can be attached to base 60 at this point.

Sizing Gauge

FIGS. 6 and 7 show an L-shaped sizing gauge 90 used for selecting the appropriate template size to accommodate the tibial head and the articular surface to be cut. Sizing gauge 90 includes a flat elongated bar 92 and a down-turned arm 94 which extends perpendicularly from one end of bar 92. As shown in FIG. 7, a contact finger 95 extends perpendicularly from arm 94 and parallels bar 92. The upper surface of bar 92 is delineated with a set of sizing indicia 96 which correspond with various sizes of templates. In addition, bar 92 has a longitudinal row of closely spaced centering holes 93 positioned between sizing indicia 96 and arm 94. Each centering hole 93 is marked with a corresponding sizing indicia 97 on the upper surface of bar 92.

In use, sizing gauge 90 is placed atop the exposed tibial head 3, as shown in FIGS. 6 and 7. Bar 92 is manually held parallelly across with contact finger 95 engaging either the lateral or medial side of tibial head 3. With the sizing gauge so positioned, the surgeon can obtain a reading to determine the appropriate template size by looking down upon the instrument as in FIG. 6. The centering hole which aligns directly over the exposed tibial head provides a size indication. A second reading is obtained from the sizing mark which overlies the lateral extremity of the tibial head. The sizing reading from the centering holes should approximately correspond to the sizing reading taken from the outside of the tibial head.

Depth Gauge

FIGS. 8–11 and 14 show the milling depth gauge 100. Depth gauge 100 includes three components: a body 102, slide 112 and lock pin 111. Generally, body 102 is shaped as shown in FIGS. 8–11. The rear side of body 102 includes a semicircular rear face 103 which extends substantially the entire length of body 102. The front side of body 102 includes a curved lower face 104 and a flat upper face 105. Lower face 104 terminates in a flat lip or intermediate face 106 which extends across the diameter of body 102. Body 102 also has a circular bottom face 107 and a semicircular top face 108. A rectangular central cavity 110 extends axially through body 102 between top face 108 and bottom face 107. A bore 109 extends from rear face 103 into cavity 110.

Slide 112 includes a ruled bar 114 and a probe 118 extending axially from one end of the bar. Ruled bar 114 has a rectangular cross section dimensioned to accommodate cavity 110. The front of ruled bar 114 is delineated with indicia 116. A longitudinal slot 115 is formed on the rear side of ruled bar 114. Probe 118 has a contact end 119. Slide 112 is fitted within body 102 for shiftable longitudinal movement within cavity 110. Ruled bar 114 extends along upper face 105 partially above lip 106 and contact end 119 extends below bottom face 107. Lock pin 111 is fitted into bore 109 and protrudes into slot 115. The movement of slide 112 is limited by pin 111 contacting the upper and lower end of slot 115.

FIG. 14 shows depth indicator 100 used in conjunction with alignment guide 10, milling base assembly 40 and template 80 to indicate amount of bone stock which will be removed during milling. Depth gauge 100 is placed on reference surface 82 of template 80 with probe 118 extending through track 84. Slide 112 is manually pushed downward through cavity 110 to contact articular surface 4 of tibial head 3. With contact end 119 in contact with articular surface 4, ruled bar 114 extends above lip 106 whereby a reading can be taken. Depth gauge 100 can be positioned at any point along track 84 in order to located the lowest point of the articular surface thereby determining the maximum cut depth.

Second Embodiment of the Milling Base

FIGS. 17–23 show a second preferred embodiment of the adjustable milling base 120. Milling base 120 operates substantially as described above but allows for bi-directional movement of the base. Adjustable milling base assembly 120 includes a T-shaped slide 130 and a shiftable base 140 connected by a pair of couplers 122. Slide 130 includes a laterally elongated head 134 and an elongated neck 132 extending perpendicularly from head 134. Neck 132 is adapted to be fitted within bore 25 of alignment guide 10. Neck 132 has a semi-circular cross section with a flat face 131 and a threaded distal end 133. Neck 132 of slide 130 is inserted into bore 25 of upper member 20 with threaded end 133 turned into vertical adjustment knob 24. Consequently, rotating vertical adjustment knob 24 extends and retracts milling base assembly 120 within upper member 20. The semi-circular cross section and flat face 131 of neck 132 keeps the milling base assembly properly aligned within bore 25 when fitted to the alignment guide.

Head 134 has two elongated openings 135 formed as shown in FIGS. 17, 20 and 22. Openings 135 are longitudinally aligned across head 134 and extend through head 134. Head 134 has two upward arms 136 which terminate in oppositely facing rails 138 which parallel head 134. As shown in FIGS. 17 and 19, rails 138 have a generally square cross section.

Shiftable base 140 has a slightly arcuate posterior face to conform to the anterior contour of the tibial head just below the knee joint. Base 140 also has a bur opening 141 to allow the burr of the milling device to pass. Two posts 142 extend perpendicularly from the anterior face of base 140. Each post 142 terminates in a raised annular lip 143. Four transverse bores 145 are formed in base 140 and extend from the anterior face to the posterior face along the lower edge of the base. As described in the first embodiment, bores 145 accommodate bone screws (not shown) to secure base 140 when properly positioned against the tibia.

Base 140 is shiftably connected to slide 130 by a pair of couplers 122. Each coupler 122 has a generally square longitudinal through bore 123 dimensioned to accommodate rails 138 and a cylindrical lateral through bore 125 dimensioned to shiftably accommodate posts 142. Couplers 122 ride on rails 138 for longitudinal movement along head 134 as shown in FIGS. 20 and 22. Posts 142 slide within bores 125 to allow base 140 to move laterally toward and away from slide 130 as shown in FIGS. 21 and 23. The connection of base 140 to slide 130 by couplers 122, allows bi-directional movement of the base with respect to the slide in a plane parallel to the articular surface of the tibial head. As shown in FIGS. 20 and 22, bores 145 in base 140 align with openings 135 in slide head 134 to accept the bonescrews which secure the base to the tibia. The width of opening 135 is sufficient to allow access to bore 145 when the base is shifted to either lateral extreme of the slide head.

Base 140 also has a pair of template mounting bores 150 and a conventional release mechanism for securing the template to the base, preferably as described for the first embodiment. The release mechanism includes two depressible release cylinders 152 shiftably housed within two end bores. Each release cylinder 152 has a lateral through bore 154 normal to its axis. Lateral bores 154 of release cylinders 152 have substantially identical diameters as mounting bores 150 and align with mounting bores 150 when release cylinders 152 are inserted into end bores. A spring (not shown) is inserted into each end bore to urge its release cylinder 152 out from its end bore, which displaces the alignment of lateral bore 154 and mounting bore 150 as shown in FIG. 18. Depressing cylinders 154 into their end bores axially realigns lateral bores 154 and mounting bores 150.

While the preceding exemplary embodiments have focused on a milling guide system for the tibial articular surface in the placement of total knee joint prosthesis, it will be understood that the techniques described are applicable to unicondylar knee replacements as well as other joints and other bone surfaces, the instrument and component geometry being adjusted accordingly. Likewise, it is understood that the above description does not limit the invention to the details given, but may be modified within the scope of the following claims.

We claim:

1. An apparatus configured for guiding a milling device for producing a planar surface on a portion of an exposed bone, said apparatus comprising:

a template means having a reference surface and defining a track for accommodating said milling device, said track extending in a anterior-posterior direction and a medial-lateral direction, said reference surface defining the amount of bone to be removed, said apparatus further including guide means configured to be secured adjacent said bone for positioning said template means over said bone portion, said template means is detachably connected to said guide means, said guide means includes alignment means for aligning said template means over said bone portion in said medial-lateral direction.

2. The apparatus of claim 1 wherein said alignment means includes a slide part adapted to be laterally secured adjacent said bone and a base part carried by said slide part in sliding engagement for longitudinal movement along said slide part, said template means is detachably connected to said base part.

3. The apparatus of claim 2 wherein said base part includes attachment means for connecting said base part to said bone when said template means is positioned over said bone portion.

4. The apparatus of claim 1 wherein said alignment means allows movement of said template means over said bone portion in two dimensions.

5. The apparatus of claim 4 wherein said alignment means includes a slide part adapted to be laterally secured adjacent said bone, a coupler carried by said slide part in sliding engagement with said slide part for movement longitudinally along said slide part, and a base part carried by said coupler in sliding engagement with said coupler for movement toward and away from said slide part, said template means is detachably connected to said base part.

6. The apparatus of claim 4 wherein said base part includes attachment means for connecting said base part to said bone when said template means is positioned over said bone portion.

7. The apparatus of claim 1 wherein said guide means also includes a shield mounted to said alignment means.

8. The apparatus of claim 1 wherein said template means includes a planar template part having said track formed therein.

9. Said apparatus of claim 1 wherein said guide means also includes an extramedullary guide secured adjacent said bone, said alignment means is extensibly connected to said extramedullary guide for movement adjacent said bone whereby said template means is spaced from said bone portion.

10. Said apparatus of claim 9 wherein said extramedullary guide includes reference means detachably connected to said extramedullary guide for proximally positioning said extramedullary guide adjacent said bone prior to securement of said extramedullary guide to said bone.

11. Said apparatus of claim 10 wherein said reference means includes a body part adapted for longitudinal connection to said extramedullary guide and a planar member extending laterally from said body part, said planar member paralleling a portion of said bone when said extramedullary guide is properly positioned with respect to said bone, said planar member includes means for centering said planar member over said bone portion when said extramedullary guide is properly positioned with respect to said bone.

12. The apparatus of claim 11 includes attachment means for extensibly connecting said body part to said extramedullary guide whereby said planar member can be spaced from said bone portion.

13. The apparatus of claim 11 wherein said planar member includes two arms extending laterally across said planar member and a marker centered between said arms, said arms and marker constituting said centering means whereby said marker overlies the center of said bone portion and each said arm extends equidistantly beyond a lateral extremity of said bone portion.

14. An apparatus used with an extramedullary alignment guide to position said extramedullary guide with respect to a bone, said apparatus comprising:

a body part adapted for longitudinal connection to said extramedullary guide and a planar member extending laterally from said body part, said planar member paralleling a portion of said bone when said extramedullary guide is properly positioned with respect to said bone, said planar member includes means for centering said planar member over said bone portion when said extramedullary guide is properly positioned with respect to said bone.

15. The apparatus of claim 14 includes attachment means for extensibly connecting said body part to said extramedullary guide whereby said planar member can be spaced from said bone portion.

16. The apparatus of claim 14 wherein said planar member includes two arms extending laterally across said planar member and a marker centered between said arms, said arms and marker constituting said centering means whereby said marker generally overlies the center of said bone portion and each said arm generally extends equidistantly beyond a lateral extremity of said bone portion.

* * * * *